United States Patent
Lugade et al.

(10) Patent No.: US 8,124,943 B1
(45) Date of Patent: Feb. 28, 2012

(54) METHODS AND SYSTEMS FOR ALTERING FLUORESCENT INTENSITIES OF A PLURALITY OF PARTICLES

(76) Inventors: Ananda G. Lugade, Austin, TX (US); Bruce J. C. Bernard, Austin, TX (US); Kurt D. Hoffacker, Austin, TX (US)

( * ) Notice: Subject to any disclaimer, the term of this patent is extended or adjusted under 35 U.S.C. 154(b) by 1363 days.

(21) Appl. No.: 11/696,771

(22) Filed: Apr. 5, 2007

Related U.S. Application Data

(60) Provisional application No. 60/744,376, filed on Apr. 6, 2006.

(51) Int. Cl.
  *G01J 1/58* (2006.01)
  *G01N 21/64* (2006.01)
  *G01N 15/02* (2006.01)
  *G01N 21/00* (2006.01)

(52) U.S. Cl. .................. 250/458.1; 250/461.2; 356/335; 356/344

(58) Field of Classification Search ............... 250/458.1, 250/459.1, 461.1, 461.2, 462.1, 483.1, 484.2, 250/486.1, 487.1, 222.1, 222.2; 356/335–338, 356/344
See application file for complete search history.

(56) References Cited

U.S. PATENT DOCUMENTS

| | | | |
|---|---|---|---|
| 4,613,559 A | | 9/1986 | Ober et al. |
| 4,979,824 A | * | 12/1990 | Mathies et al. ............... 356/318 |
| 5,315,122 A | * | 5/1994 | Pinsky et al. ............... 250/461.2 |
| 5,682,038 A | * | 10/1997 | Hoffman .................... 250/458.1 |
| 5,736,330 A | | 4/1998 | Fulton |
| 5,981,180 A | | 11/1999 | Chandler et al. |
| 6,046,807 A | | 4/2000 | Chandler |
| 6,057,107 A | | 5/2000 | Fulton |
| 6,139,800 A | | 10/2000 | Chandler |
| 6,268,222 B1 | | 7/2001 | Chandler et al. |
| 6,366,354 B1 | | 4/2002 | Chandler |

(Continued)

FOREIGN PATENT DOCUMENTS

WO  00/63695  10/2000

OTHER PUBLICATIONS

Wedekind et al., "Scanning microphotolysis: a new photobleaching technique based on fast intensity modulation of a scanned laser beam and confocal imaging," Journal of Microscopy, vol. 176, Pt. 1, Oct. 1994, pp. 23-33.

(Continued)

*Primary Examiner* — Georgia Y Epps
*Assistant Examiner* — Don Williams
(74) *Attorney, Agent, or Firm* — Fulbright & Jaworski L.L.P.

(57) ABSTRACT

A method for altering fluorescent emissions of particles includes setting the particles in motion and exposing the moving particles to light such that fluorescent intensities of the particles are lessened isotropically and substantially simultaneously. Another method includes measuring fluorescent emissions of particles, determining the measured fluorescent emissions do not collectively fit within a first predetermined range of fluorescent values, and exposing the particles to one or more incidents of light that are configured to cooperatively alter the fluorescent emissions of the particles to be within a second predetermined range of fluorescent values. An embodiment of an apparatus includes a vessel configured to contain a plurality of particles and a means for setting the particles in motion. The apparatus further includes an illumination subsystem configured to direct light toward the vessel and at a spectral window (i.e., wavelength or band of wavelengths) which is configured to isotropically and substantially simultaneously lessen the fluorescent emissions of each of the particles.

20 Claims, 3 Drawing Sheets

Setting a plurality of fluorescent particles in motion — 30

Exposing the moving particles to light such that fluorescent intensities of the particles are lessened isotropically across each of the particles and simultaneously among the particles — 32

U.S. PATENT DOCUMENTS

| | | |
|---|---|---|
| 6,411,904 B1 | 6/2002 | Chandler |
| 6,449,562 B1 | 9/2002 | Chandler et al. |
| 6,514,295 B1 | 2/2003 | Chandler et al. |
| 6,524,793 B1 | 2/2003 | Chandler et al. |
| 6,528,165 B2 | 3/2003 | Chandler |
| 6,599,331 B2 | 7/2003 | Chandler et al. |
| 6,632,526 B1 | 10/2003 | Chandler et al. |
| 6,649,414 B1 | 11/2003 | Chandler et al. |
| 2003/0220549 A1* | 11/2003 | Liu et al. ............. 600/317 |
| 2004/0069857 A1 | 4/2004 | Leblans et al. |
| 2006/0105395 A1 | 5/2006 | Pempsell |

OTHER PUBLICATIONS

Braeckmans et al., "Encoding microcarriers by spatial selective photobleaching," Nature Materials, vol. 2, Mar. 2003, pp. 169-173.

Horak et al., "Preparation of Colored Poly(styrene-co-butyl methacrylate) Micrometer Size Beads with Narrow Size Distribution by Dispersion Polymerization in Presence of Dyes," Journal of Polymer Science: Part A: Polymer Chemistry, vol. 33, 1995, pp. 2961-2968.

\* cited by examiner

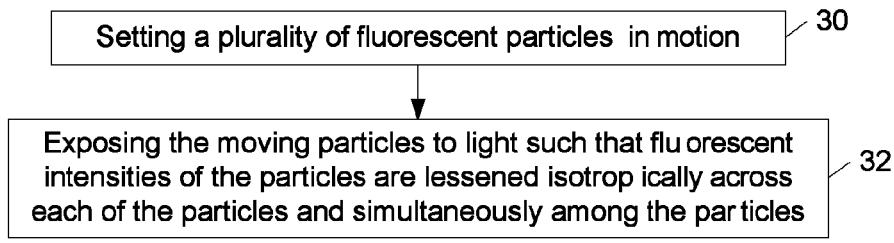
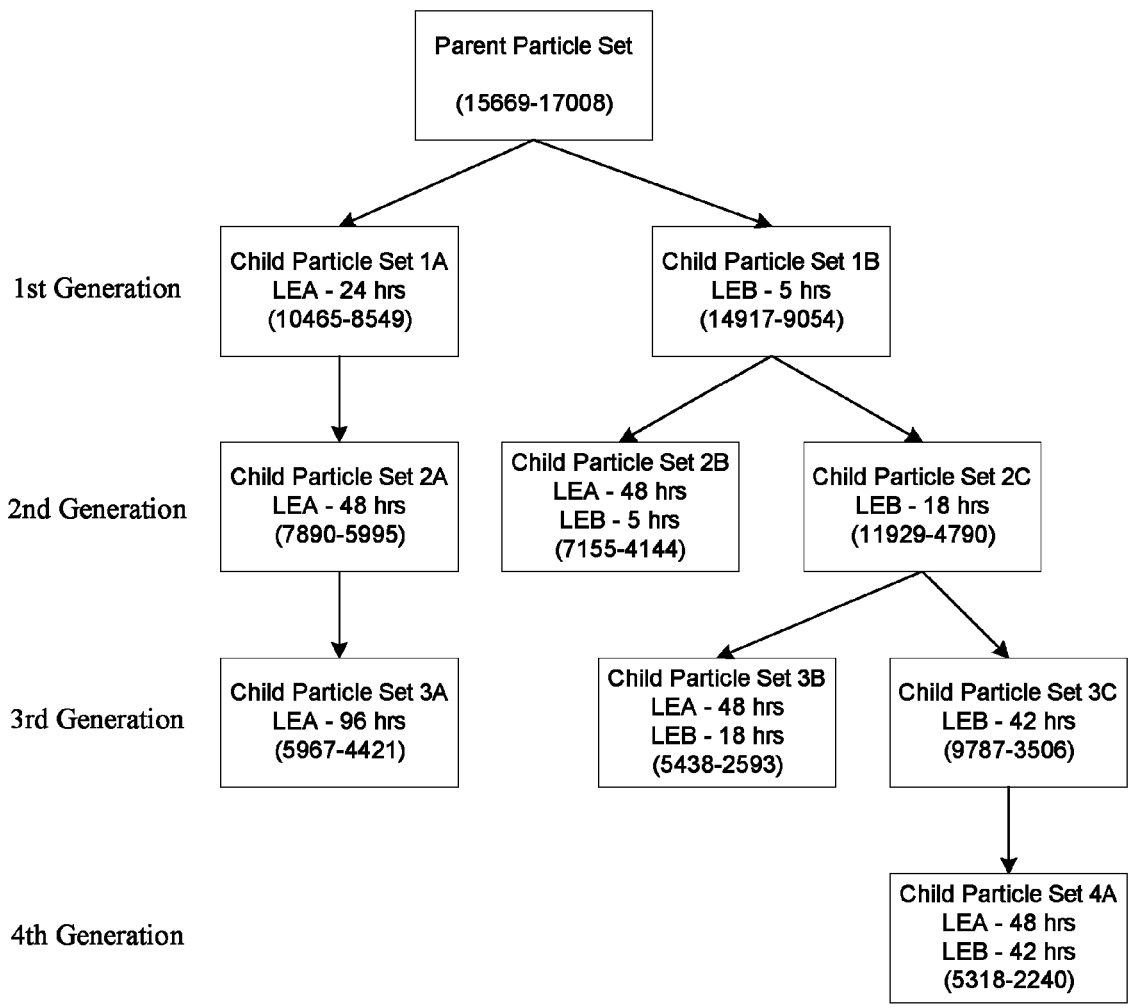

METHODS AND SYSTEMS FOR ALTERING FLUORESCENT INTENSITIES OF A PLURALITY OF PARTICLES

BACKGROUND OF THE INVENTION

1. Field of the Invention

This invention generally relates to methods and apparatuses for encoding particles and, more specifically, to methods and systems for altering fluorescent intensities of a plurality of particles.

2. Description of the Related Art

The following descriptions and examples are not admitted to be prior art by virtue of their inclusion within this section.

Spectroscopic techniques are widely employed in the analysis of chemical and biological systems. Most often, these techniques involve measuring the absorption or emission of electromagnetic radiation by the material of interest. One application is in the field of microarrays, which is a technology exploited by a large number of disciplines including the combinatorial chemistry and biological assay industries. Luminex Corporation of Austin, Tex. has developed systems in which biological assays, for example, are performed on the surface of variously colored fluorescent particles. In such systems, a multiplexing scheme is often employed in which multiple analytes are evaluated in a single sample. To facilitate a multiplexing scheme, particles are often configured into distinguishable groups. For instance, different fluorescent dyes as well as different concentrations of dyes may be absorbed into particles and/or bound to the surface of particles. In one example, employing two dyes at 10 different concentrations among a set of particles produces 100 fluorescently distinguishable particle categories. The number of particle categories may be augmented by increasing the number of dyes and/or different dye intensities. For example, if 15 different dye intensities were possible rather than 10 in the aforementioned example, then 225 particle categorizations would be achievable. The inclusion of additional dyes and/or dye intensities, however, adds complexity to the system, which can greatly contribute to increasing the expense and/or difficulty of producing the platform.

In any case, dyes are generally chosen based on their ability to emit light at a wavelength of a selected detection window. The detection windows define the different particle categories and are typically spaced apart by a certain number of wavelengths. In general, the dyes are designed to minimize the overlap of a dye's fluorescent signal within adjacent windows. In this manner, the different particle categorizations may be sufficiently distinguishable. In some cases, however, it may be difficult to produce particles exhibiting fluorescent intensities which fall into predetermined detection windows. As such, it may theoretically possible to produce hundreds of particle categories, but in practice such a number of categories is difficult to achieve. One factor that may limit the number of particle categories that can be produced may be the controllability of the methods used to dye the particles (e.g., how well variations of the process parameters of the methods can be minimized, the predictability of the methods to produce dyed particles of particular fluorescent intensities, and the degree to which parameters of the methods can be altered to produce desired fluorescence emissions). Furthermore, dyed particles may not exhibit expected fluorescence emissions for a number of other reasons including varying characteristics (e.g., size and/or composition) of the particles prior to being dyed. In any case, particles that exhibit fluorescence emissions that do not fit within a selected detection window are typically scrapped or discarded, increasing the time and expense of producing a population of particles for a multiplexing scheme.

Accordingly, it would be advantageous to develop methods and systems for altering fluorescence emissions of dyed particles. Such methods and systems may be particularly beneficial for encoding particles with specific fluorescent intensities and/or adjusting the fluorescent intensity of a particle which does not fall within a predetermined detection window.

SUMMARY OF THE INVENTION

The following description of various embodiments of systems and apparatuses for altering fluorescent intensities of a plurality of particles is not to be construed in any way as limiting the subject matter of the appended claims.

An embodiment of a method for altering fluorescent emissions of particles includes setting a plurality of the particles in motion and exposing the moving particles to light such that fluorescent intensities of the particles are lessened isotropically and substantially simultaneously.

An embodiment of another method for altering fluorescent emissions of particles includes measuring fluorescent emissions of particles having one or more integrated fluorescent materials and determining the measured fluorescent emissions do not collectively fit within a first predetermined range of fluorescent values. The method further includes exposing the particles to one or more incidents of light that are configured to cooperatively alter the fluorescent emissions of the particles to be within a second predetermined range of fluorescent values.

An embodiment of an apparatus for altering fluorescent emissions of particles includes a vessel configured to contain a plurality of particles and a means for setting particles contained within the vessel in motion. The apparatus further includes a subsystem with a light source system and an optical system collectively configured to direct light toward the vessel and at a spectral window (i.e., wavelength or band of wavelengths) which is configured to isotropically and substantially simultaneously lessen the fluorescent emissions of each of the particles contained within the vessel.

BRIEF DESCRIPTION OF THE DRAWINGS

Other objects and advantages of the invention will become apparent upon reading the following detailed description and upon reference to the accompanying drawings in which:

FIG. 1 is a flowchart of a method for photo-bleaching a plurality of particles isotropically and simultaneously;

FIG. 2 is a tree-structure of an exemplary photo-bleaching scheme used to generate a plurality of particle classifications from a parent set of particles and further from different child sets of particles;

Figure 3:
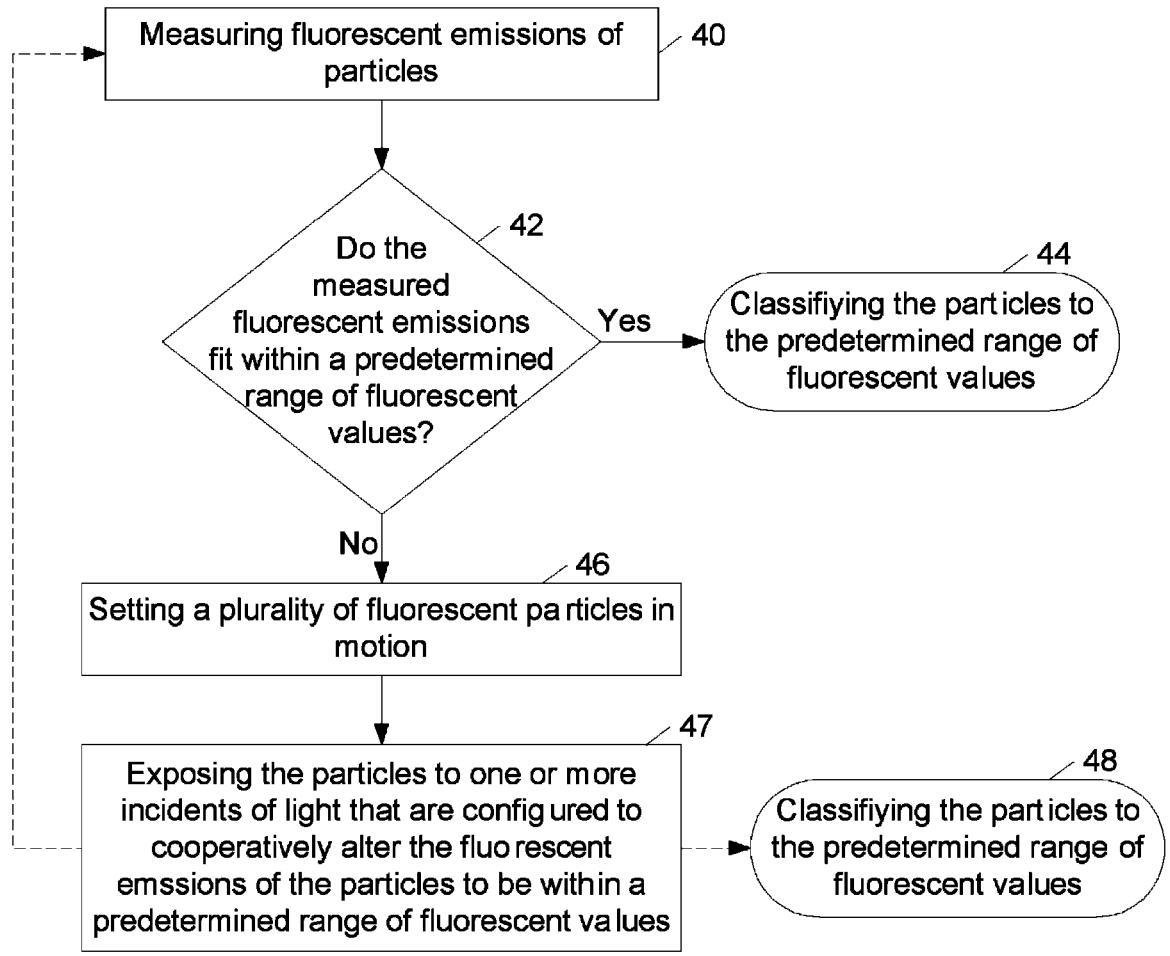
FIG. 3 is a flowchart of a method for altering fluorescence emissions of a plurality of particles to fit within a predetermined range of fluorescent values.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 5:
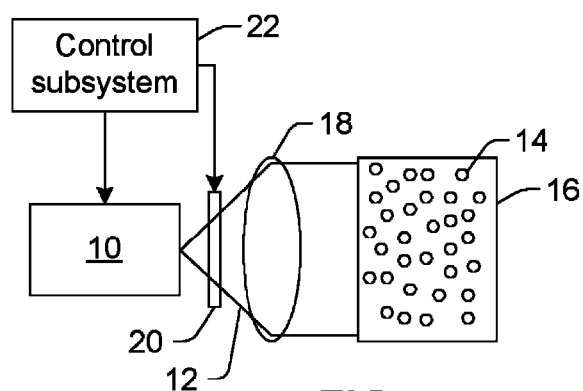
FIG. 5 is a schematic diagram of a system configured to photo-bleach a plurality of particles isotropically and simultaneously.

Turning to the drawings, exemplary methods and systems for altering fluorescent intensities of a plurality of particles are shown. In particular, FIGS. 1 and 3 illustrate flowcharts of exemplary methods and FIG. 5 illustrates a schematic diagram of an exemplary system for performing such methods. FIG. 4 depicts scatter plots of exemplary data illustrating the repositioning of an improperly coded particle set into a proper classification space using the methods and FIG. 2 depicts a tree-diagram for implementing the methods to facilitate a large number of particles classifications.

In general, the term "particle" as used herein may refer to any substrate used for the analysis of chemistry and biological assays and may specifically refer to articles used to provide and/or support molecular reactions for the qualification and/or quantification of an analyte of interest. In addition, the term "particle" may reference articles of a broad range of sizes, such as but not limited to articles having dimensions between approximately 1 nm approximately 300 μm. Hence, the term "particle" may refer to a number of different materials and configurations, including but not limited to microspheres, polystyrene beads, microparticles, gold nanoparticles, quantum dots, nanodots, nanoparticles, composite particles (e.g., metal-polymeric particles or magnetite-polymeric particles), nanoshells, nanorods, nanotubes, beads, microbeads, latex particles, latex beads, fluorescent beads, fluorescent particles, colored particles, colored beads, tissue, cells, micro-organisms, spores, organic matter, any non-organic matter, or any combination thereof. Accordingly, any of such terms may be interchangeable with the term "particle" used herein. Furthermore, although embodiments are described herein with respect to dyed particles, it is to be understood that the embodiments described herein may be used with particles having any photoluminescent material (e.g., a fluorophore or a quantum dot).

As shown in block 30 of FIG. 1, the method described herein may include setting a plurality of fluorescent particles in motion. In addition, the method may include block 32 in which the moving particles are exposed to light such that fluorescent intensities of the particles are lessened isotropically across each of the particles and substantially simultaneously among the particles. In general, the process outlined in block 30 for setting the plurality of particles in motion may be performed in any manner sufficient to evenly expose the entirety of the particles' surfaces to light that is used to alter the fluorescence of the particles (i.e., the light used to expose the moving particles referenced in block 32). Evenly exposing the entirety of the particles' surfaces to light may advantageously insure that the fluorescence of each particle is isotropically reduced (i.e., the fluorescence of each particle is evenly reduced over substantially the whole particle). As such, the manner in which the particles are set in motion may depend on the configuration of the illumination system used to alter the fluorescence of the particles and/or the vessel used to contain the particles as described in more detail below. Consequently, the process of setting the particles in motion may vary among systems. Exemplary processes that may be used to set particles in motion may include but are not limited to stirring/agitating the particles in a suspension medium (i.e., a liquid or a gas) and/or shaking/vibrating/rotating the vessel containing the particles.

In addition to facilitating a fluorescence reduction isotropically across each of the particles, the method outlined in FIG. 1 may include limiting the areal coverage of the particles' movement in block 30 relative to the areal coverage of the light exposure in block 32 such that the reduction of fluorescence among the particles may be performed substantially simultaneously. More specifically, the process for setting the plurality of particles in motion and/or components of the system used to perform the method outlined in FIG. 1 may be configured to insure the particles are not set in motion outside the span of the light exposure used to reduce the fluorescence of the particles. In this manner, the reduction of fluorescence among the particles may be conducted concurrently. In some embodiments, the process for setting the plurality of particles in motion and/or components of the system used to perform the method outlined in FIG. 1 may be configured to process a relatively large number of particles at the same time. For example, the methods described herein may be performed on about $10^7$ particles to about $10^{10}$ particles at a time.

The process of exposing the moving particles to light in block 32 of FIG. 1 includes exposing the particles to light spectrally configured to render molecules of one or more fluorescent materials within and/or on the particles substantially incapable of emitting fluorescence. As a consequence, upon illumination of the particles by one or more excitation sources of a fluorescence measurement system, the particles exhibit lower fluorescence. In addition to being wavelength dependent, the number of molecules rendered incapable of emitting fluorescence is proportional to the length of time of the light exposure, the light intensity and the nature of the luminophore. Therefore, all or less than all of the molecules of the one or more fluorescent materials may be rendered incapable of emitting fluorescence depending on the time specifications of the exposure. In some cases, the light may be spectrally configured to render molecules of one or more fluorescent materials substantially incapable of emitting fluorescence more than another photoluminescent material within and/or on a particle. In particular, each photoluminescent material may be configured to have a different wavelength of peak absorption. With judicious control of the wavelengths of the source light, molecules of one or more of the photoluminescent materials within and/or on a particle can be preferentially rendered incapable of emitting fluorescence versus another photoluminescent material. In this manner, exposure of particles to the source light may selectively render molecules only one or fewer than all of the photoluminescent materials included within or on the particle incapable of emitting fluorescence.

In general, the process of rendering molecules of fluorescent materials substantially incapable of emitting fluorescence may be conducted either by direct photon absorption of light or via energy transfer from another molecule. The reduction of fluorescence among particles correlates to color fading of the particles and, thus, the process may be referred to as photo-bleaching. In addition or alternatively, the reduction of fluorescence may be referred to as "erasing" a portion of one or more photoluminescent materials integrated with the particles or "subtractive dyeing." As described above, the process and/or system used to perform the method described herein are configured to perform the photo-bleaching process isotropically and simultaneously among a plurality of particles as well as selectively with respect to one or more fluorescent materials integrated with the particles and, therefore, the process described herein may be more specifically referred to as selective isotropic photo-bleaching.

The selective isotropic photo-bleaching process described herein may be applied to fluorescent materials that are absorbed within the particles and/or bound to the exterior surfaces of particles. Consequently, the reference used herein of the one or more fluorescent materials being "integrated" with the particles may generally refer to either or both scenarios. In some embodiments, it may be particularly advantageous to employ particles having fluorescent materials bound to the exterior surfaces of particles since it is believed that such particle configurations may be bleached slightly faster. In either case, since the selective isotropic photo-bleaching methods described herein are performed using particles having one or more integrated fluorescent materials, the method described herein may include integrating the fluorescent materials with the particles prior to setting the particles in motion with reference to block 30 in FIG. 1. In some embodiments, it may be advantageous to employ non-covalent or hydrophobic techniques for the integration process since they are easily impregnated inside a hydrophobic microsphere. As noted above, the methods described herein may be used with particles having any photoluminescent material (e.g., a dye or a fluorophore) and, as such, the process of integrating particles with fluorescent materials may include any processes for integrating dyes or fluorophores within and/or on particles.

Examples of suitable methods for dyeing particles are illustrated and described in U.S. Pat. No. 6,632,526 to Chandler et al., which is incorporated by reference as if fully set forth herein. In particular, a method of staining polymeric microspheres with two or more fluorescent dyes is disclosed by Chandler et al. The method includes combining at least two fluorescent dyes in a mixture having at least one organic solvent with which at least two fluorescent dyes are soluble and at least one alcoholic solvent with which at least two fluorescent dyes are less soluble. The resulting solution is characterized as having the capacity to swell but not dissolve the polymer microspheres. The method includes contacting the polymeric microspheres with the solution for a period of time sufficient to provide uniform staining of substantially all of the polymeric microspheres with at least two fluorescent dyes. It is noted that the aforementioned method by Chandler et al. is exemplary and, therefore, should not necessarily be construed to limit the methods described herein. In particular, other methods for dyeing particles (including dyeing one or a plurality of dyes within and/or on particles) and/or methods for incorporating fluorophores within and/or on particles may be considered for the integration processes described herein.

An advantage of the selective isotropic photo-bleaching methods described herein is that resulting particles may be classified or "encoded" based on fluorescent intensities integrated over substantially the whole particle. In other words, the methods described herein may generate a fluorescent "code" by which to identify the particles. In some embodiments, the method outlined in FIG. 1 may be conducted for a number of different sets of particles, with each of the sets exposed to different incidents of light (i.e., different wavelengths of light and/or lengths of time of light exposure). In this manner, a plurality of different particle classifications may be generated. Such an embodiment may be particularly advantageous for a multiplexing assay, for example. The different sets of particles may initially fit within the same fluorescence emission range and, therefore, the generation of different classifications may be referred to as generating new "child" or "daughter" codes from a "parent" fluorescent code.

In addition to generating a plurality of particle classifications from a parent set of particles, the method outlined in FIG. 1 may be applied to child sets of particles to generate additional child particle classifications. An example of such a scheme is illustrated in FIG. 2 and described in more detail below. As noted above, the methods described herein may, in some embodiments, include exposing light which is spectrally configured to photo-bleach one or more fluorescent materials preferentially over another photoluminescent material within and/or on a particle. Although the methods do not necessarily need to incorporate such preferential exposure, such a technique may advantageously increase the number of possible particle classifications which may be generated from a parent set of particles and, as such, a larger number of particle classifications may be generated.

FIG. 2 illustrates a tree structure of an exemplary photo-bleaching scheme used to generate a plurality of particle classifications from a parent set of particles and further from different child sets of particles. Each block of the tree structure represents a different particle set, with the top block of the tree structure representing the parent particle set and the other blocks representing child particle sets. As shown by the arrows in the tree structure, a first generation of child particle sets may be generated from the parent particle set and further generations of child particle sets may be generated from previously generated child particle sets. Fewer than all of the particles in a set may be used to generate additional child particle sets and, therefore, each block may represent a particle classification. In this manner, the scheme outlined in FIG. 2 may generate up to 10 different particle classifications. Each block of the child particle sets outlines the incidents of light exposure used to generate the given particle set as well as mean fluorescence intensity (MFI) values recorded at the end of the exposure for each photoluminescent material integrated within and/or on the particles. In particular, the blocks outline exposure times of two different wavelength applications, respectively noted as light exposure A (LE-A) and light exposure (LE-B). In addition, the blocks outline resulting MFI values for two different photoluminescent materials integrated within and/or on the particles (i.e., the MFI values are in parentheses and separated by a hyphen).

It is noted that the scheme outlined in FIG. 2 is exemplary and, consequently, the methods described herein should be not limited by the depiction of FIG. 2. In particular, any number of child particle sets may be generated from a previously generated particle set and, therefore, the methods described herein are not limited to the generation of one or two particle sets from a previously generated particle set as shown in FIG. 2. In addition, the methods described herein are not limited at producing 4 generations of child particle sets and, thus, an indefinite number of particle classifications may be generated using the hierarchical scheme described herein. Moreover, the MFI values presented in FIG. 2 are exemplary and, therefore, should not be construed to limit the methods described herein particularly with reference to the type of fluorescent materials integrated with the particles. Furthermore, the exposure times of the photo-bleaching applications are exemplary in FIG. 2 and, likewise, should not limit the scope of the methods described herein. In particular, any length of exposure times may be considered for the methods described herein including but not limited to exposure times of less than approximately 1 hour, less than approximately 5 minutes, less than approximately 1 minute, as well as multiple hours as noted in FIG. 2. Moreover, although the scheme outlined in FIG. 2 depicts the use of two different wavelengths of light exposure, any number of different wavelength applications may be used for the generation of a particle set.

In addition or alternative to creating a plurality of different particle classifications, the method outlined in FIG. 1 may be used to correct a particle set that has been integrated with an improper amount of fluorescent material. In particular, particles are often encoded into different classification groups by integrating specific amounts of fluorescent material. More specifically, fluorescent materials are generally selected such that upon excitation of the particles of a fluorescence measurement system, a distinct fluorescence signal is emitted from the particles. The intensity of the emitted signal is proportional to the amount of the fluorescent materials in the particles. In some cases, however, it may be difficult to produce particles having specific concentrations of fluorescent materials and, therefore, it may be difficult to produce particles exhibiting a specific range of fluorescent emissions. Such particle sets may be referred to herein as being "improperly encoded" or "incorrectly coded." The method outlined in FIG. 1, however, may be used to move improperly encoded set of particles into a proper location of a classification space by controlled exposure to light. A flowchart of an exemplary process for correcting particle encoding is illustrated in FIG. 3. FIGS. 4A-4F illustrate the progression of correcting an incorrectly coded particle set into a proper classification space using the method outlined in FIG. 3 and, therefore, is described in conjunction with FIG. 3.

As shown in block 40 of FIG. 3, the method may include measuring the fluorescent emissions of a set of particles. Such a measurement process may be performed by any known measurement process, such as by flow cytometry or fluorescence imaging. The method continues to block 42 in which a determination is made as to whether the measured fluorescent emissions fit within a predetermined range of fluorescent values. FIGS. 4A-4F illustrate exemplary scatter plots with eight oval regions representing distinct particle classifications. Each axis of the scatter plots represents a range of MFI values of a different fluorescent material and, therefore, each of the oval regions represents a predetermined range of fluorescent values which is deemed acceptable for the given particle classification. It is noted that the scatter plots illustrated in FIGS. 4A-4F are exemplary and, therefore, the methods described herein are not necessarily restricted to the depiction of FIGS. 4A-4F. In particular, the methods described herein may be applied to classification spaces having any number, shape and size of classification regions.

Turning back to FIG. 3, upon determining the measured fluorescent emissions fit within a predetermined range of fluorescent values, the method continues to block 44 in which the particle set is classified to the predetermined range of fluorescent values. Conversely, if it is determined that the measured fluorescent emissions do not fit within a predetermined range of fluorescent values, the method continues to blocks 46 and 47 to alter the fluorescent emissions of the particles to be within a predetermined range of fluorescent values. Such a process may be similar to the sequence of steps described in reference to FIG. 1. For the sake of brevity, the descriptions of the processes described in FIG. 1 are referenced for blocks 46 and 47 and are not reiterated here. A distinction of block 47 in FIG. 3 versus block 32 in FIG. 1 is that the light exposure is specifically configured to alter the fluorescent emissions of the particles to be within a predetermined range of fluorescent values. In particular, the process of altering the fluorescence of the particles is preferably performed such that the particles may be classified to a particle classification region.

In some cases, the process outlined in block 47 of FIG. 3 may involve a single exposure of light. In other cases, the exposure process may involve a series of light exposures. The plurality of light exposures (i.e., incidents) may include the same or different wavelengths (or spectral window) of light and/or the same or different periods of time. In some embodiments, the different incidents of light may be successively conducted without substantial processing therebetween. In other cases, the fluorescence emissions of at least some of the particles may be measured in between at least some of the incidents of light until it is determined that the particles fit within a predetermined range of fluorescent values. In such cases, the method depicted in FIG. 3 may loop through blocks 40, 42, 46 and 47 and finally to block 44 to classify the particles to a predetermined range of fluorescent values. A dotted line is shown in FIG. 3 between blocks 47 and 40 to illustrate such an embodiment is optional. In other cases, a determination of the number, duration and spectral window (i.e., wavelength or band of wavelengths) of light exposure needed to alter fluorescence emissions of the particles to fit within a predetermined range of fluorescent values may be automated. The automated determination may be based upon historical data and/or simulation programs and, as such, measurement of the fluorescent emissions of the particles after exposure to the light may not be needed. In such embodiments, the method may continue to block 48 to classify the particles to the predetermined range of fluorescent values.

Figure 4A:
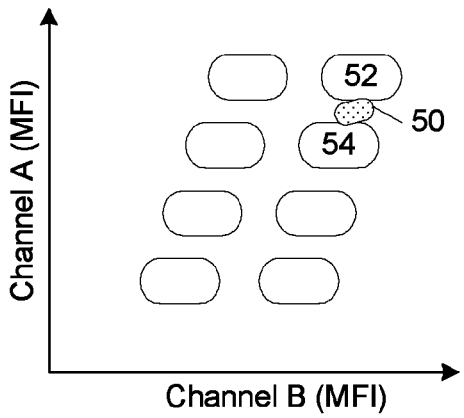
FIGS. 4A-4F depict a series of scatter plots illustrating the progression of correcting an incorrectly coded particle set into a proper classification space.
Figure 4B:
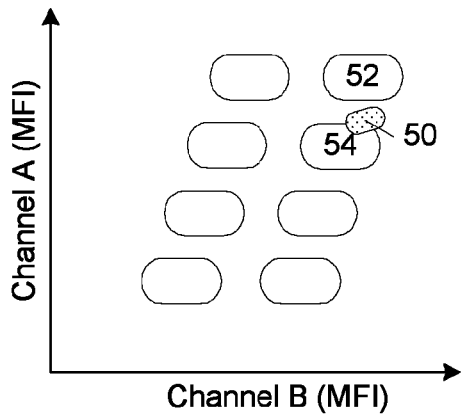
Figure 4C:
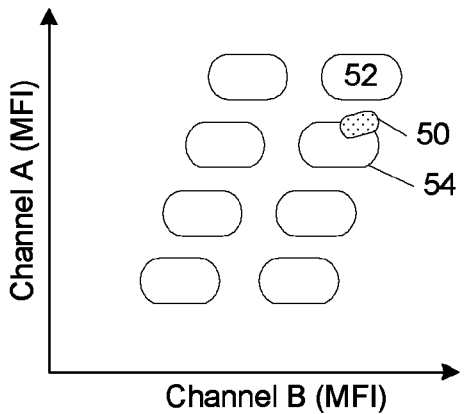
Figure 4D:
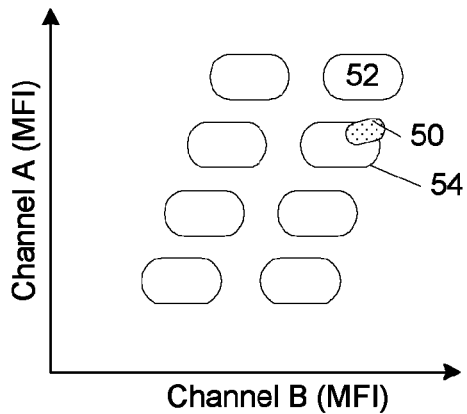
Figure 4E:
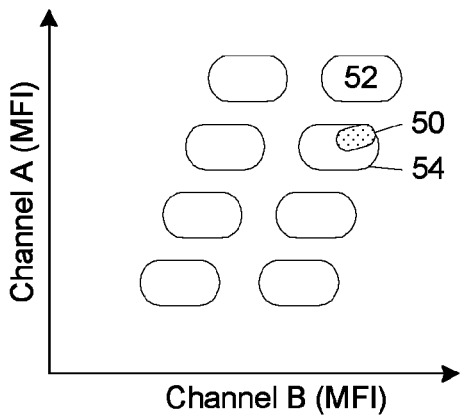
Figure 4F:
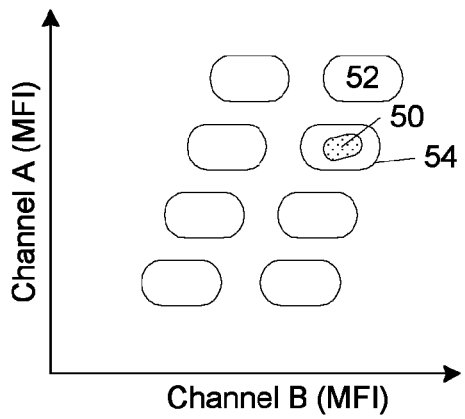

FIG. 4A illustrates an exemplary scatter plot graphing particle fluorescence for a set of particles incorrectly coded with a fluorescent material. In particular, FIG. 4A illustrates particle set 50 having a range of particle fluorescence values between particles classification regions 52 and 54. Since particle set 50 does not fit in either classification region, it is rendered improperly coded and unsuitable for use. FIGS. 4B-4F illustrate an exemplary progression of fluorescence changes among particle set 50 after different incidents of light exposures. As shown in FIGS. 4B-4F, the different incidents of light has altered the fluorescence of particle set 50 to fit within a particle classification region, notably classification region 54. It is noted that the duration of light exposure needed to correct an improperly coded particle set may be significantly shorter than the duration of light exposure suggested to generate child particle sets from previously generated particle sets in FIG. 2. In particular, the duration of exposure for the incidents of light in block 47 may be on the order of a few minutes or less and, in some cases, less than approximately 1 minute.

As noted above in reference to block 32 of FIG. 1, the photo-bleaching process renders one or more molecules of a photoluminescent material incapable of emitting fluorescence and, therefore, lessens the fluorescence of the material. For this reason, the correction of improperly coded particles will generally be made to fit the particles within a region of lower fluorescence that what was incorrectly coded onto the particles. In cases in which particles are coded with more fluorescent material than intended, the correction of the particles may move the particle set into the intended classification region. However, in cases in which particles are coded with less fluorescent material than intended, the correction of the particles will need to move the particle set into a classification region other than what was originally intended.

FIG. 5 illustrates an exemplary system for altering fluorescence emissions of a plurality of particles. The system includes light source 10 configured to emit light 12. As shown in FIG. 5, light 12 may be directed through optical elements 18 and 20 to particles 14 disposed within vessel 16. Light source 10 may include one or more light sources such as any suitable light emitting diodes (LEDs), lasers, arc lamps, fiber illuminators, light bulbs, incandescent lamps, or any other suitable light sources known in the art. The light source(s)

may be selected to provide light 12 at wavelength(s) or wavelength band(s) capable of rendering one or more molecules of one or more photoluminescent materials integrated with particles 14 substantially incapable of emitting fluorescence such that upon illumination of the particles by one or more excitation sources, the particles exhibit lower fluorescence emissions. If the particle includes two or more photoluminescent materials, light source 10 and wavelength of light 12 may be configured such that one or more molecules of only one of the photoluminescent materials (or of fewer than all of the photoluminescent materials) is rendered substantially incapable of emitting fluorescence. Alternatively, light source 10 and wavelengths of light 12 may be configured such that one or more molecules of all of the photoluminescent materials integrated with particles 14 are rendered substantially incapable of emitting fluorescence. Consequently, light source 10 and the wavelengths of light 12 may be configured based on the photoluminescent materials integrated with particles 14.

In general, light source 10 may include any number of the aforementioned light sources, including multiple sources of the same type of light source or different light sources. One example of an appropriate combination of light sources which may be particular useful for the system shown in FIG. 5 includes, but is not limited to, two or more LEDs, particularly green and red LEDs. In particular, green and red LEDs may offer light at a sufficient spectral window (i.e., wavelength or band of wavelengths) to allow the system to be void of spectral filters, simplifying the system. Alternatively, a relatively bright light source such as a 400 W medium pressure mercury lamp commercially available from Hanovia Ltd. of Slough, England, may be advantageous to facilitate faster alteration or correction of the fluorescence emissions of the particles.

In some cases, light generated from more than one light source may be combined into a common illumination path by a beamsplitter or any other suitable optical element known in the art. Alternatively, light source 10 may be configured to illuminate the particles at different directions. In some embodiments, the system may include an optical element (other than optical elements 18 and 20 described below) such as a reflecting mirror and a device configured to move the optical element into and out of the illumination path depending on which light source is used to illuminate particles 14. In this manner, the light sources may be used to sequentially illuminate particles 14 with different wavelengths or wavelength bands of light (e.g., blue light and green light). As such, light source 10 may be configured such that the light directed to the particles is monochromatic, near monochromatic, polychromatic, or broadband. In any case, although the system in FIG. 5 is shown to direct light 12 to vessel 16 at a substantially normal angle of incidence, it is to be understood that the system may be configured to direct the light to vessel 16 at any other suitable angle of incidence.

Light source 10 together with optical element 18 and/or optical element 20 may constitute an illumination subsystem. Optical element 18 may include any suitable optical element known in the art to direct light such as a collimating lens. Although optical element 18 is shown in FIG. 5 as a single refractive optical element, optical element 18 may include one or more refractive optical elements and/or one or more reflective optical elements. Optical element 20 may be any suitable optical element configured to alter one or more characteristics of light 12 emitted by light source 10. For instance, optical element 20 may be a spectral filter that alters the wavelength(s) of light 12. In another example, optical element 20 may be a neutral density filter or other filter that alters the intensity of light 12. In yet another example, optical element 20 may be a polarizing component that alters the polarization of light 12. Optical element 20 may include any appropriate spectral filter, neutral density filter, or polarizing component known in the art.

Although the system is shown in FIG. 5 as including one of each type of optical element (i.e., optical elements 18 and 20), the system may include more than one of each type of optical elements. Furthermore, although optical element 20 is shown as being disposed between light source 10 and optical element 18, it is to be understood that optical element 20 may alternatively be disposed between optical element 18 and vessel 16. Alternatively, the system may not include one or both of optical elements 18 and 20. In some cases, the system may include one or more other optical elements such as a diffuser or a homogenizer to increase the uniformity of the light directed across the illumination area or volume of the system (i.e., across the area or volume of the particles illuminated by the light).

Vessel 16 may include any suitable container that is relatively transparent to light and is configured to contain a plurality of particles. In this manner, the system may be configured to alter the fluorescence emissions of particles 14 on a batch-by-batch basis. In addition, the system may be configured to alter one or more fluorescence emission characteristics of particles 14 substantially simultaneously. Vessel 16 may include a mechanism or means for setting particles 14 in motion (e.g., a vibration or mixing mechanism) such that the particles move within the container while the fluorescence emissions of the particles are being altered. Such movement of the particles within the vessel may increase the uniformity of the altered fluorescence emissions across each of the particles. The vessel may have any suitable shape and size. Although vessel 16 is shown in FIG. 5 as a single container, vessel 16 may include two or more separate containers or two or more compartments that may each contain a separate population of particles. In this manner, multiple populations of particles may be encoded or corrected simultaneously, particularly in embodiments in which light source 10 is configured to emit light at different wavelengths. As shown in FIG. 5, light 12 is directed to vessel 16 in which multiple particles 14 are disposed such that multiple particles are exposed to light 12 substantially simultaneously.

As shown in FIG. 5, the system may further include control subsystem 22 operatively coupled to light source 10 and, in some cases, operatively coupled to optical element 20. In general, control subsystem 22 may be configured to automate the operations of the system and, more specifically, control light source 10 and/or optical element 20 to produce specific wavelengths or wavelength bands of light 12. In some embodiments, control subsystem 22 may be configured to produce specific wavelengths or wavelength bands of light 12 based upon measured fluorescence emissions of particles 14, such as for the method described in FIG. 3. In addition to controlling light source 10 and/or optical element 20, control subsystem 22 may configured to provide a precise wavelength or wavelength band by means of a plurality of filters or a "bank of filters." The filters can be moved mechanically into position by electric motors or by an operator. Then, by switching the exposure between different filters, the bleaching rate can be monitored and controlled as desired. Several companies such as Chroma Tech, Rockingham, Vt., or OMEGA Optical, Brattleboro, Vt., can generate custom optics (filters, dichroic mirrors, etc.) that are suitable for a targeted bleaching strategy. After generating the bleaching "trail" for specific photoluminescent materials, a more standardized approach toward exposure time and filter selection can be adopted for the photo-beaching process. As noted above, control subsystem 22 may be automated and, thus, may serve as a storage medium having program instructions which are executable by a process to control light source 10, optical element 20, and or the aforementioned "bank of filters."

In some embodiments, the system shown in FIG. 5 for altering fluorescence emissions of a plurality of particles may be operatively coupled to a system used to measure fluorescence emissions of particles. For example, a fluorescent measurement system may, in some embodiments, be coupled to an inlet of vessel 16. In such cases, the apparatus of coupled systems may be configured to supply at least some of particles 14 from the fluorescent measurement system to vessel 16 after initial measurement of the particles. In some embodiments, the apparatus may additionally or alternatively include a return line coupled between an outlet of vessel 16 and a staging section of the fluorescent measurement system. In this manner, at least some of particles 14 may be routed to the fluorescent measurement system to check the progress of the photo-bleaching process. In cases in which there is a recirculation loop integrated between the systems, the progress of the photo-bleaching process may be checked any number of times and particles 14 may be passed back to vessel 16 for further photo-bleaching based upon the measurements of fluorescence emissions.

The following examples are not to be considered limiting embodiments of the invention and are included herein for example purposes only.

EXAMPLE 1

Alteration of Fluorescence Emissions of a Plurality of Particles

Particles were each dyed with both Dye A and Dye B to form a parent particle set. In this example, 2,4-bis[2,4-dimethylpyrrole]cyclobutenediylium-1,3-dioxolate served as "Dye A" and 2,4-bis[1,1-dimethyl-2-(1-H-benz[e]indolinylidenemethyl)]cyclobutenediylium-1,3-dioxolate served as "Dye B". Other dyes, however, may be used with the photo-bleaching process described herein. The fluorescent emissions of the particles were measured using a Luminex 100 instrument available from Luminex Corporation of Austin, Tex. The fluorescent intensities for each dye are given in units of MFI with the intensity of Dye A reported by the A channel and the intensity of dye B reported by the B channel. The parent particle set was exposed to various light conditions in order to generate different regions by selective photo-bleaching. One subset of the parent particle set was diluted to 500,000 microspheres/mL and photo-bleached using a red LED. Samples were taken at various time points. The MFI values for this subset are reported in Table 1.

TABLE 1

| # of minutes of exposure to red LED | MFI Dye B | MFI Dye A |
| --- | --- | --- |
| 0 | 16647 | 17645 |
| 10 | 11669 | 16840 |
| 20 | 9375 | 16497 |
| 34 | 7761 | 15955 |
| 50 | 6530 | 15313 |
| 75 | 5407 | 14608 |
| 110 | 4263 | 13670 |
| 155 | 3506 | 12728 |

A second subset of the parent particle set was diluted to 500,000 microspheres/mL and photo-bleached using a green LED. Samples were taken at various time points. The MFI values for this subset are reported in Table 2.

TABLE 2

| # of minutes of exposure to green LED | MFI Dye B (Channel B) | MFI Dye A (Channel A) |
| --- | --- | --- |
| 0 | 17450 | 16815 |
| 3 | 16139 | 15254 |
| 10 | 14271 | 12836 |
| 15 | 13062 | 11446 |
| 30 | 10920 | 8696 |
| 45 | 9083 | 6980 |
| 60 | 8310 | 6351 |
| 92 | 6764 | 5151 |
| 120 | 5612 | 4424 |
| 180 | 4361 | 3701 |
| 210 | 3853 | 3424 |
| 380 | 2577 | 2717 |

A number of the particle subpopulations with different light exposure times listed in Tables 1 and 2 were mixed together with the parent population. The selected subpopulations are distinct and could be used in a multiplexing system.

EXAMPLE 2

Correction of Fluorescence Emissions of a Plurality of Particles

After encoding a subset of the encoded particles, they are tested against the predefined fluorescent targets. If a set of encoded particles does not fit any of the predefined targets, the set cannot be used in combination with other sets that are targeted correctly. However, using small exposures of light, the population of particles may have their fluorescent emissions altered to be within one of the predefined spaces. In an exemplary embodiment referencing the scatter plots of FIGS. 4A-4F, exposure to a red LED moves the improperly encoded particle population down the channel B axis while exposure to a green LED moves the population diagonally down both the channel A and channel B axes. The following sequence of light exposures was used in such an example to move the particle population within a predefined space. It is noted that such a sequence of exposures is exemplary and, therefore, the methods described herein are not necessarily so limited.

1. starting population
2. after 1 minute exposure to red LED
3. after additional 1 minute exposure to red LED
4. after another additional 1 minute exposure to red LED
5. after additional 1 minute exposure to green LED
6. after another additional 2 minute exposure to green LED It will be appreciated to those skilled in the art having the benefit of this disclosure that this invention is believed to provide methods and systems for altering fluorescence emissions of a plurality of particles. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this descrip-

What is claimed is:

1. A method for altering fluorescent emissions of particles, comprising:
setting a first plurality of particles in motion; and
exposing the moving first plurality of particles to light such that fluorescent emissions of the first plurality of particles are lessened isotropically across each of the plurality of particles and substantially simultaneously among the plurality of particles.

2. The method of claim 1, wherein the step of exposing the moving first plurality of particles comprises exposing the moving first plurality of particles to light spectrally configured to lessen fluorescent intensity of one fluorescent material integrated with the first plurality of particles more than another fluorescent material integrated with the first plurality of particles.

3. The method of claim 1, further comprising:
setting one or more different pluralities of particles in motion independent of setting the first plurality of particles in motion; and
exposing each of the different pluralities of moving particles to a different set of light emissions such that:
fluorescent emissions of particles within each of the different pluralities of particles are lessened substantially simultaneously and isotropically; and
the range of fluorescent emissions among the exposed different pluralities of particles are distinct from each other and the exposed first plurality of particles.

4. The method of claim 3, further comprising encoding different groups of particles to have different concentrations of one or more fluorescent materials prior to setting the first plurality of particles and the different pluralities of particles in motion.

5. The method of claim 4, wherein the first and different pluralities of the particles are selected from one of the encoded groups of particles, and wherein the method further comprises:
placing one or more discrete sets of particles in motion independent of setting the first plurality of particles and the one or more different pluralities of particles in motion, wherein the one or more discrete sets of particles are selected from one or more of the other encoded groups of particles; and
exposing the one or more discrete sets of particles to light such that:
fluorescent emissions of particles within each of the discrete sets of particles are lessened substantially simultaneously and isotropically; and
the range of fluorescent emissions among the exposed discrete sets of particles are distinct from each other as well as the exposed first plurality of particles and the exposed one or more different pluralities of particles.

6. The method of claim 4, wherein the step of encoding the different groups of particles comprises hydrophobically dying the different groups of particles.

7. A method for altering fluorescent emissions of particles, comprising:
measuring fluorescent emissions of particles having one or more integrated fluorescent materials;
determining the measured fluorescent emissions of the particles do not collectively fit within a first predetermined range of fluorescent values; and
exposing the particles to one or more incidents of light that are configured to cooperatively lessen the fluorescent emissions of the particles to be within a second predetermined range of fluorescent values.

8. The method of claim 7, wherein the first and second predetermined ranges of fluorescent values are different ranges of fluorescent values.

9. The method of claim 7, wherein the first and second predetermined ranges of fluorescent values are the same range of fluorescent values.

10. The method of claim 7, wherein the step of exposing the particles to one or more incidents of light comprises exposing the particles to a different spectral window of light.

11. The method of claim 7, further comprising measuring fluorescent emissions of at least some of the particles between incidents of light exposure.

12. The method of claim 7, wherein the step of exposing the particles to one or more incidents of light comprises successively exposing the particles to different incidents of light without substantial processing therebetween.

13. The method of claim 7, wherein the one or more incidents of light are collectively configured to alter the fluorescent emissions of the particles isotropically across each of the particles and substantially simultaneously among the particles.

14. The method of claim 7, wherein the one or more fluorescent materials are adhered to exterior surfaces of the particles.

15. An apparatus for altering fluorescent emissions of particles, comprising:
a vessel configured to contain a plurality of particles;
a means for setting particles contained within the vessel in motion; and
a subsystem comprising a light source system and an optical system collectively configured to direct light toward the vessel and at a spectral window which is configured to isotropically and substantially simultaneously lessen the fluorescent emissions of each of the particles contained within the vessel.

16. The apparatus of claim 15, wherein the light source system comprises at least one of a red light emitting diode (LED) and a green LED.

17. The apparatus of claim 15, wherein the light source system comprises a mercury lamp.

18. The apparatus of claim 15, further comprising a control system operatively coupled to the light source system and the optical system, wherein the control systems comprises program instructions which are executable by a processor for:
automatically determining the spectral window of light based upon measured fluorescent emissions of the particles; and
controlling the light source system and the optical system to apply the determined spectral window of light.

19. The apparatus of claim 15, further comprising a fluorescent measurement system coupled to an inlet of the vessel, wherein the apparatus is configured to pass at least some of the particles from the fluorescent measurement system to the vessel.

20. The apparatus of claim 19, further comprising a return line coupled between an outlet of the vessel and a staging section of the fluorescent measurement system.

* * * * *

UNITED STATES PATENT AND TRADEMARK OFFICE
CERTIFICATE OF CORRECTION

PATENT NO.         : 8,124,943 B1                                                Page 1 of 1
APPLICATION NO.    : 11/696771
DATED              : February 28, 2012
INVENTOR(S)        : Ananda G. Lugade It is certified that error appears in the above-identified patent and that said Letters Patent is hereby corrected as shown below:

Title Page, item 73

Add to Assignee, Luminex Corporation, 12212 Technology Dr., Austin, TX 78727

Signed and Sealed this
Fifth Day of June, 2012

David J. Kappos
*Director of the United States Patent and Trademark Office*